US008871190B2

(12) United States Patent
Marshall et al.

(10) Patent No.: US 8,871,190 B2
(45) Date of Patent: Oct. 28, 2014

(54) POLYMERIC PHEROMONE FORMULATION AND METHOD OF USE TO CALM STRESS-RELATED BEHAVIOR IN MAMMALS OVER AN EXTENDED PERIOD OF TIME

(71) Applicant: Sergeant's Pet Care Products, inc., Omaha, NE (US)

(72) Inventors: Gerald Marshall, Athens, TX (US); Larry Nouvel, Plano, TX (US); Cuong Tu Ba, Miami, FL (US); Luis Rios, Pembroke Pines, FL (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

(21) Appl. No.: 13/688,997

(22) Filed: Nov. 29, 2012

(65) Prior Publication Data

US 2013/0116220 A1     May 9, 2013

Related U.S. Application Data

(63) Continuation-in-part of application No. 12/430,075, filed on Apr. 25, 2009, now abandoned, and a continuation-in-part of application No. 12/877,911, filed on Sep. 8, 2010, now abandoned, and a continuation-in-part of application No. 12/974,565, filed on Dec. 21, 2010.

(51) Int. Cl.
*A01N 25/00* (2006.01)
*A61K 31/575* (2006.01)
*A61K 31/01* (2006.01)
*A61K 31/201* (2006.01)
*A61K 31/045* (2006.01)
*A61K 31/20* (2006.01)
*A61K 31/194* (2006.01)
*A61K 47/06* (2006.01)
*A61K 47/32* (2006.01)
*A61K 9/00* (2006.01)
*A61K 47/34* (2006.01)

(52) U.S. Cl.
CPC .............. *A61K 31/575* (2013.01); *A61K 31/01* (2013.01); *A61K 31/201* (2013.01); *A61K 31/045* (2013.01); *A61K 31/20* (2013.01); *A61K 31/194* (2013.01); *A61K 47/06* (2013.01); *A61K 47/32* (2013.01); *A61K 9/0014* (2013.01); *A61K 9/007* (2013.01); *A61K 47/34* (2013.01)
USPC ............................. 424/84; 424/405; 424/406

(58) Field of Classification Search
CPC ... A61K 9/007; A61K 9/0014; A61K 31/201; A61K 31/01; A61K 47/06; A61K 47/10; A61K 47/12; A61K 47/30; A61K 47/32; A61K 47/34
See application file for complete search history.

(56) References Cited

U.S. PATENT DOCUMENTS 6,077,867 A    6/2000   Pageat
6,169,113 B1   1/2001   Pageat
(Continued)

OTHER PUBLICATIONS

Tod E et al: "Efficacy of dog appeasing pheromone in reducing stress and fear related behaviour in shelter dogs", Applied Animal Behaviour Science, Elsevier Science Publishers BV., Amsterdam, NL. vol. 93. No. 3-4, Mar. 17, 2005, pp. 295-308. XPo27662809, ISSN: 0168-1591.

(Continued)

*Primary Examiner* — Bethany Barham
(74) *Attorney, Agent, or Firm* — Polsinelli PC

(57) ABSTRACT

Pheromone compositions comprising a combination of squalene, linoleic acid and 1-docosanol are described, along with methods of using the pheromone compositions to modify behavior in mammals. The compositions are useful for behavior modification in mammals that exhibit undesirable or harmful stress-related behaviors.

32 Claims, 2 Drawing Sheets

(56) References Cited

U.S. PATENT DOCUMENTS

| | | |
|---|---|---|
| 6,372,242 B1 | 4/2002 | Gutierrez |
| 6,384,252 B1 | 5/2002 | Pageat |
| 7,901,695 B2 | 3/2011 | Chao |
| 7,960,461 B2 | 6/2011 | Lin |
| 2007/0225379 A1 | 9/2007 | Carrara et al. |
| 2008/0008731 A1 | 1/2008 | Hurwitz |

OTHER PUBLICATIONS

Veterinary Products Laboratories, "Veterinary Products Laboratories introduces first ever Dog Appeasing Pheromone Collar", press release [online, May 4, 2006], <URL:www.vpl.com/press/view_press.pho?id=100693>.

US 8,871,190 B2

POLYMERIC PHEROMONE FORMULATION AND METHOD OF USE TO CALM STRESS-RELATED BEHAVIOR IN MAMMALS OVER AN EXTENDED PERIOD OF TIME

CROSS REFERENCE TO RELATED APPLICATION

This application is a continuation-in-part of U.S. Nonprovisional application Ser. No. 12/430,075 filed on Apr. 25, 2009, of U.S. Nonprovisional application Ser. No. 12/877,911 filed on Sep. 8, 2010, and of U.S. Nonprovisional application Ser. No. 12/974,565 filed on Dec. 21, 2010, the disclosures of which are hereby incorporated by reference in their entirety.

FIELD OF THE INVENTION

The present invention generally relates to a pheromone composition comprising squalene, linoleic acid, and 1-docosanol, which composition is useful for appeasing mammals, and is particularly useful for modifying objectionable behaviors in domestic animals that result from stress or anxiety. The present invention is further directed to a polymeric pheromone formulation comprising a low melting-point polymer or copolymer, a saturated or unsaturated long chain fatty alcohol, and a pheromone composition comprising squalene, linolenic acid, and 1-docosanol.

The present invention is further directed to an animal behavioral control system and method of use wherein the system comprises a polymeric pheromone formulation present in a device that is worn by or placed on a mammal and which allows for the slow-release of the appeasing pheromone. More specifically, the system of the present invention is placed on or in close proximity to an animal to be treated and it releases the appeasing pheromone over an extended period of time of about four weeks or longer.

BACKGROUND

A pheromone is a chemical signaling compound naturally produced by many animals that elicits a predictable and specific behavioral response in another member of the same species. Pheromone compounds and functions vary and are thought to include alarm pheromones, food trail pheromones, reproductive pheromones, and probably many others affecting animal behavior. Although originally and most well documented in insect species, pheromones are the subject of increasing study with recognition growing regarding the role that pheromones play in modifying the behavior of mammalian species.

In mammals pheromones are thought to be detected by olfactory membranes or by the vomeronasal organ (VNO or Jacobson's organ), which is positioned between the nose and mouth and functions as the first stage of the accessory olfactory system. However, unlike regular olfactory membranes, the VMO is connected directly to the mid-brain and thus enjoys the shortest organ-to-brain distance in mammals. This feature allows pheromones present in extremely small quantities to selectively trigger certain biochemical processes in the animal. Moreover, pheromone signals go directly to subconscious areas of brain without being processed by the conscious brain, and thus pheromone effects are both rapid and subconscious. While the precise mechanisms underlying pheromone effects on the mammalian brain remain to be further explored and characterized, a growing body of evidence indicates clear behavioral effects likely involving at least hormonal responses. For example, studies of the house mouse have revealed a complex pheromone communication system for signaling inter-male aggression and dominance, mating readiness, and for signaling stress to the other members of the colony. All of these behaviors have demonstrated correlations with hormonal pathways. Pheromone effects may also be mediated by basic olfactory mechanisms and behavioral effects associated with olfactory processing. For example, olfactory processing is known to be important for newborn mammals. Newborns, including humans, can identify the mother from her scent. This process may be crucial to bonding and survival and is thought a likely candidate for involving pheromone mechanisms in mammals. Thus, growing evidence is consistent with an important role for pheromones in controlling mammalian behavior, and particularly those behaviors associated with bonding, socialization, aggression, and stress.

In domestic, farm, and zoo animals, including dogs, cats, horses, swine, cattle, tigers, lions, bears, elephants, etc., fear and anxiety arising from various sources frequently result in harmful or annoying behaviors that are not well tolerated by the affected animal, other animals or human owners/handlers. For example, separation anxiety in dogs frequently results in soiling, excessive chewing or licking, property destruction, constant barking, and hyperactivity. Pet cats under stress, for instance, from the introduction of a new cat to the household, will often spray, scratch, claw, and make other displays of aggression. Generally, a need is recognized for compositions and methods that can be used on any affected domestic, farm, or zoo animal to control such undesirable behaviors.

It is an object of the present invention to develop an animal behavioral control system and device that can be worn by an animal to be treated with the pheromone composition and which is always in the presence of an animal in order to provide a consistent and long-term behavior treatment regimen to an animal exhibiting stress-related behavior disorders. However, because the pheromone compositions of the present invention contain a blend of natural fatty acids, it can be difficult to prepare a solid polymeric delivery device for use with the pheromone compositions. The necessity for including high amounts of fatty acids in the polymeric article can lead to undesirable results, such as the formation of fatty acid oil residue on the surface of the device, release rates of the pheromone composition that are unacceptably fast, the production of polymeric articles that are too soft and can easily be pulled apart with tension, or polymeric material that cannot be extruded at high or low temperatures. Therefore, it is an object of the present invention to prepare solid polymeric delivery devices, such as collars, ear tags, or the like, that does not extrude the components at high temperatures, but rather processes the ingredients under conditions of lower temperature than are normally used in the art of polymeric extrusion.

SUMMARY OF THE INVENTION

The inventors have unexpectedly found novel pheromone compositions that are useful for modifying behavior in mammals, and are particularly useful for modifying objectionable behaviors in domestic animals that result from stress or anxiety. The compositions are based in part on the surprising finding that squalene-based compositions (i.e. compositions comprising squalene in an amount equal to at least 30% by weight of the composition) are effective at modifying stress- or anxiety-related behaviors in domestic animals. All percents provided herein are percent by weight based on the total weight of the composition (% w/w) unless otherwise indicated.

In one aspect there is provided a pheromone composition for modifying behavior in a mammal, the composition comprising squalene, linoleic acid, and 1-docosanol.

In another aspect there is provided a pheromone composition for modifying behavior in a mammal, the composition comprising squalene in an amount equal to between about 20% and about 40% by weight of the composition, linoleic acid in an amount equal to between about 50% and about 70% by weight of the composition, and 1-docosanol in an amount equal to between about 1% and about 10% by weight of the composition.

In another aspect there is provided a pheromone composition comprising squalene in an amount equal to between about 60% and about 70% by weight, linoleic acid in an amount equal to between about 15% and about 25% by weight, 1-docosanol in an amount equal to between about 1% and about 5% by weight, and a mixture of at least two fatty acids in an amount equal to between about 5% and about 15% by weight, wherein the fatty acids are selected from the group consisting of myristic acid, n-pentadecanoic acid, lauric acid, azelaic acid, pimelic acid, and combinations thereof.

In another aspect there is provided a pheromone composition for modifying behavior of a mammal, the pheromone composition comprising squalene in an amount equal to between about 20% and about 40% by weight, linoleic acid in an amount equal to between about 50% and about 70% by weight, 1-docosanol in an amount equal to between about 1% and about 5% by weight, cholesterol in an amount equal to between about 0.1% and about 5% by weight, and a mixture at least two fatty acids in an amount equal to between about 1% and about 10% by weight, wherein the fatty acids are selected from the group consisting of myristic acid, n-pentadecanoic acid, lauric acid, and combinations thereof.

In another aspect there is provided a pheromone composition for modifying behavior of a mammal, the pheromone composition comprising squalene in an amount equal to between about 20% and about 40% by weight, linoleic acid in an amount equal to between about 55% and about 65% by weight, 1-docosanol in an amount equal to between about 1% and about 5% by weight, cholesterol in an amount equal to between about 0.1% and about 5% by weight, and a mixture at least two fatty acids in an amount equal to between about 1% and about 5% by weight, wherein the fatty acids are selected from the group consisting of myristic acid, n-pentadecanoic acid, lauric acid, and combinations thereof.

In yet another aspect there is provided a pheromone composition for modifying behavior of a mammal, the pheromone composition comprising squalene in an amount equal to between about 20% and about 40% by weight, linoleic acid in an amount equal to between about 50% and about 70% by weight, 1-docosanol in an amount equal to between about 1% and about 10% by weight, cholesterol in an amount equal to between about 1% and about 10% by weight, and a mixture at least two fatty acids in an amount equal to between about 1% and about 5% by weight, wherein the fatty acids are selected from the group consisting of myristic acid, n-pentadecanoic acid, lauric acid, and combinations thereof.

In another aspect there is provided a pheromone composition comprising squalene in an amount equal to between about 60% and about 70% by weight, linoleic acid in an amount equal to between about 15% and about 25% by weight, 1-docosanol in an amount equal to between about 1% and about 5% by weight, cholesterol in an amount equal to between about 0.1% and about 5% by weight, and a mixture of at least two fatty acids in an amount equal to between about 5% and about 10% by weight, wherein the fatty acids are selected from the group consisting of myristic acid, n-pentadecanoic acid, lauric acid, azelaic acid, capric acid, pimelic acid, and combinations thereof.

In a further aspect there is provided a pheromone solution for modifying behavior of a mammal, the solution comprising an organic solvent in an amount equal to between about 70% and about 90% by volume of the solution and a pheromone composition as disclosed herein in an amount equal to between about 1% and about 40% by volume of the solution.

In another aspect there is provided a method of modifying stress-related behavior in a mammal, the method comprising administering to the mammal a therapeutically effective amount of a pheromone composition as disclosed herein.

In a further aspect there is provided a solid polymeric formulation for controlling behavior in mammals comprising a pheromone composition as disclosed herein, a saturated or unsaturated long chain fatty alcohol of from about 11 to about 18 carbon atoms, and a low melting polymer or copolymer. The polymeric formulation described herein is useful for making articles or devices such as animal collars, tags, solid diffusers, and the like. These articles or devices are also encompassed by the present invention and can be used for releasing the pheromone composition to a local environment in contact with the animal, over an extended or prolonged period of time. By "extended or prolonged period of time" is meant for a period of activity longer than the period of activity exhibited by the raw active ingredient alone. The extended period of release can be for at least two weeks, more preferably, at least three weeks, and most preferably at least four weeks.

DETAILED DESCRIPTION OF THE INVENTION

Figure 1:
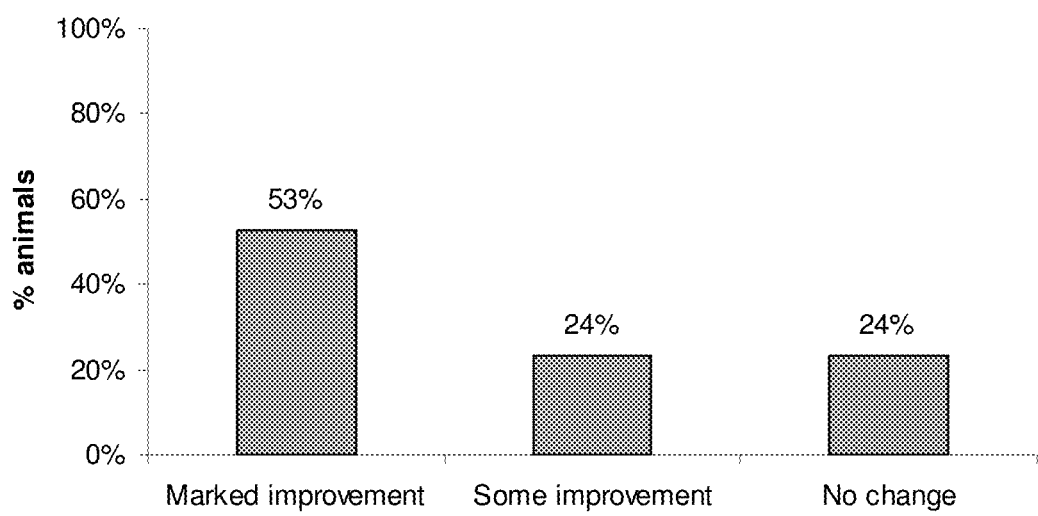
FIG. 1 is a bar graph illustrating the behavioral results obtained in a study of the effects on behavior of an exemplary pheromone composition on dogs exhibiting behavior problems.

The pheromone compositions provided herein are believed to mimic certain naturally occurring pheromones that have a calming or appeasing effect on mammals. As such, the compositions are useful for controlling behavior in mammals and are especially useful for controlling stress- or anxiety-induced behavior in pets and domestic animals such as, but not limited to, dogs, cats, and horses. In particular, the pheromone compositions disclosed herein are based in part on the unexpected finding that compositions made primarily from squalene, a naturally occurring organic compound obtained from shark liver oil, and certain volatile organic compounds including certain fatty acids, demonstrate calming effects on mammals. Accordingly, the term "squalene-based" as used herein to describe the pheromone compositions refers to a composition that includes at least 30% by weight of squalene. Most surprisingly, such compositions were found to produce strong calmative effects in mammals without additionally including either palmitic acid or oleic acid, two fatty acids that are necessary components in previously described pheromone compositions, such as, for example, in U.S. Pat. No. 6,077,867 and U.S. Pat. No. 6,384,252.

I. Compositions

A basic pheromone composition of the present invention comprises squalene, linoleic acid, and 1-docosanol (behenyl alcohol or docosyl alcohol), with the balance of the composition being comprised of cholesterol and/or a mixture of at least two fatty acids selected from the group consisting of myristic acid, n-pentadecanoic acid, lauric acid, capric acid, azelaic acid, pimelic acid, and combinations thereof.

Squalene is a natural organic compound originally obtained for commercial purposes primarily from shark liver oil, but is also derived from botanical sources, including amaranth seed, rice bran, wheat germ, and olives. As derived from shark liver oil, squalene is readily available from many commercial sources. The amount of squalene present in the pheromone composition may be equal to from about 20% to about 80% by weight of the composition. For example, squalene may be present in the pheromone composition in an amount equal to about 20%, 25%, 30%, 35%, 40%, 45%, 50%, 55%, 60%, 65%, 70%, 75%, or 80% by weight of the composition. In one embodiment, squalene may be present in an amount equal to between about 20% and about 50% by weight of the composition, preferably between about 20% and about 40% by weight of the composition, and more preferably between about 30% and about 40% by weight of the composition. In another embodiment, squalene may be present in an amount equal to between about 50% and about 80% by weight of the composition, preferably in amount equal to between about 50% and about 70% by weight of the composition, and most preferably in an amount equal to between about 60% and about 70% by weight of the composition.

Linoleic acid is an omega-6-fatty acid, used in the biosynthesis of arachidonic acid (AA) and some prostaglandins. It is found in the lipids of cell membranes. It is abundant in many vegetable oils, especially safflower and sunflower oils. Similarly, linoleic acid is also available from a variety of commercial sources. The amount of linoleic acid present in the pheromone composition may be equal to from about 10% to about 80% by weight of the composition. For example, the pheromone composition may comprise linoleic acid in an amount equal to about 10%, 15%, 20%, 25%, 30%, 35%, 40%, 45%, 50%, 55%, 60%, 65%, 70%, 75%, or 80% by weight of the composition. In one embodiment, linoleic acid is present in the composition in an amount equal to between about 10% and about 40% by weight of the composition, preferably in an amount equal to between about 15% and about 30% by weight of the composition, and more preferably in an amount equal to between about 15% and 25% by weight of the composition. In another embodiment, linoleic acid is present in the pheromone composition in an amount equal to between about 40% and about 80% by weight of the composition, preferably in an amount equal to between about 50% and about 70% by weight of the composition, and more preferably in an amount equal to between about 55% and about 65% by weight of the composition.

1-docosanol (also known as n-docosanol, docosyl alcohol, behenic alcohol behenyl alcohol, Cachalot BE-22, Dehydag wax 22 (lanette), Emery 3304, and Loxiol VPG 1451) is a carboxylic acid generally known for antiviral therapeutic properties, and its use in the treatment of cold sores. Like squalene and linoleic acid, 1-docosanol is available from a variety of commercial sources. The amount of 1-docosanol present in the pheromone composition may be equal to from about 1% to about 10% by weight of the composition. For example, the pheromone composition may comprise 1-docosanol in an amount equal to about 1%, 2%, 3%, 4%, 5%, 6%, 7%, 8%, 9%, or 10% by weight of the composition.

In one embodiment, 1-docosanol is present in the composition in an amount equal to between about 1% and about 5% by weight of the composition, preferably in an amount equal to between about 1% and about 3% by weight of the composition. In another embodiment, 1-docosanol is present in the pheromone composition in an amount equal to between about 2% and about 10% by weight of the composition, preferably in an amount equal to between about 3% and about 6% by weight of the composition.

Cholesterol is generally a steroid found in the cell membranes which is transported in the blood plasma of most animals. Cholesterol is an important precursor molecule for the biosynthesis of bile acids, steroid hormones, and several other fat-soluble vitamins. One skilled in the art will appreciate that the cholesterol component of the current invention is available from a variety of commercial sources. The amount of cholesterol present in the pheromone composition may be equal to from about 0.1% to about 10% by weight of the composition. For example, the pheromone composition may comprise cholesterol in an amount equal to about 0.1%, 0.2%, 0.3%, 0.4%, 0.5%, 1%, 2%, 3%, 4%, 5%, 6%, 7%, 8%, 9%, or 10% by weight of the composition. In one embodiment, cholesterol is present in the composition in an amount equal to between about 0.1% and about 5% by weight of the composition, preferably in an amount equal to between about 0.5% and about 3% by weight of the composition. In another embodiment, cholesterol is present in the composition in an amount equal to between about 1% and about 10% by weight of the composition, preferably in an amount equal to between about 2% and about 8% by weight of the composition, and more preferably in an amount equal to between about 3% and about 6% by weight of the composition.

A mixture of at least two fatty acids may further be included in the pheromone composition and these fatty acids can be used in pure form, i.e., as a free fatty acid or in a derivative form such as an ester, salt, alcohol, ketone, ether or amide. Fatty acids are commercially readily available from various chemical companies, typically in solid form. To dissolve a fatty acid obtained in solid form, the fatty acid is typically added to a solvent under constant agitation and at an elevated temperature of about 37° C. to about 38° C. A fatty acid can also be microencapsulated and suspended in water to form a water suspension.

Fatty acids suitable for inclusion in the mixture of at least two fatty acids include propanoic acids such as propionic acid; butanoic acids such as butyric acid; pentanoic acids such as valeric acid; hexanoic acid such as caproic acid; heptanoic acids such as enanthic acid; octanoic acids such as caprylic acid; nonanoic acids such as pelargonic acid; decanoic acids such as capric acid; undecanoic acids such as undecylic acid; dodecanoic acids such as lauric acid; tridecanoic acids such as tridecylic acid; heptadecanoic acids such as margaric acid; octadecanoic acids such as stearic acid; eicosanoic acids such as arachidic acid; heneicosanoic acids such as heneicosylic acid; tricosanoic acids such as tricosylic acid; tetracosanoic acids such as lignoceric acid; pentacosanoic acids such as pentacosylic acid; hexacosanoic acids such as cerotic acid; heptacosanoic acids such as heptaosylic acid; octacosanoic acids such as montanic acid; nonacosanoic acids such as nonacosylic acid; triacontanoic acids such as melissic acid; henatriacontanoic acids such as henatriacontylic acid; dotriacontanoic acids such as lacceroic acid; tritriacontanoic acids such as psyllic acid; tetratriacontanoic acids such as geddic acid; pentatriacontanoic acids such as ceroplastic acid; hexatriacontanoic acids such as hexatriacontylic acid; nonanedioic acids such as azelaic acid; tetradecanoic acids such as myristic acid; pentadecyclic acids such as n-pentadecanoic acid; and heptanedioic acids such as pimelic acid. Derivatives of these fatty acids such as esters or salts can also be used in the composition.

It is preferred that if a fatty acid mixture is included in the pheromone composition, at least two additional fatty acids are present. Preferably, the mixture of fatty acids comprises fatty acids selected from the group consisting of myristic acid, n-pentadecanoic acid, lauric acid, capric acid, azelaic acid, pimelic acid, and combinations thereof. The mixture of at least two fatty acids specifically excludes both palmitic acid and oleic acid. In one embodiment, the mixture of fatty acids comprises myristic acid, n-pentadecanoic acid, and lauric acid. In a second embodiment, the mixture of fatty acids comprises myristic acid, n-pentadecanoic acid, lauric acid, azelaic acid and pimelic acid. In a third embodiment, the mixture of fatty acids comprises myristic acid, n-pentadecanoic acid, lauric acid, capric acid, azelaic acid, and pimelic acid.

The mixture of at least two fatty acids present in the pheromone composition may be equal to from about 1% to about 15% by weight of the composition. For example, the pheromone composition may comprise a mixture of at least two fatty acids in an amount equal to about 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 12%, 13%, 14%, or 15% by weight of the composition. In one embodiment, the pheromone composition comprises a mixture of fatty acids in an amount equal to between about 1% and about 5% (% w/w), wherein fatty acids are selected from the group consisting of myristic acid, n-pentadecanoic acid, lauric acid, capric acid, azelaic acid, pimelic acid, and combinations thereof. In another embodiment, the pheromone composition comprises a mixture of fatty acids in an amount equal to between about 5% and about 10% (% w/w), wherein fatty acids are selected from the group consisting of myristic acid, n-pentadecanoic acid, lauric acid, capric acid, azelaic acid, pimelic acid, and combinations thereof. In yet another embodiment, the pheromone composition comprises a mixture of fatty acids in an amount equal to between about 10% and about 15% (% w/w), wherein fatty acids are selected from the group consisting of myristic acid, n-pentadecanoic acid, lauric acid, capric acid, azelaic acid, pimelic acid, and combinations thereof.

The amount of myristic acid present in the pheromone composition may be equal to between about 0.5% and about 5% by weight of the composition, preferably between about 0.5% and about 3% by weight, and most preferably between about 1% and about 1.6% by weight.

The amount of n-pentadecanoic acid present in the pheromone composition may be equal to between about 0.1% and about 10% by weight, preferably between about 0.5% and about 7% by weight.

The amount of lauric acid present in the pheromone composition may be equal to between about 0.1% and about 1% by weight, preferably between about 0.1% and about 0.5% by weight.

The amount of azelaic acid present in the pheromone composition may be equal to between about 0.5% and about 5% by weight, preferably between about 1% and about 3% by weight.

The amount of pimelic acid present in the pheromone composition may be equal to between about 0.5% and about 5% by weight, preferably between about 1% and about 3% by weight.

The amount of capric acid present in the pheromone composition may be equal to between about 1% and about 8% weight, preferably between about 2% and about 5% by weight.

The pheromone composition may optionally include other components such as amines, glycol, glycerol, and non-toxic lipophilic anti-oxidants such as butylated hydroxytoluene ("BHT", also known as butylhydroxytoluene). In a preferred embodiment, the pheromone composition comprises butylated hydroxytoluene in an amount equal to between about 0.001% and about 1% by weight of the composition, preferably between about 0.005% and about 0.05% by weight. The basic pheromone composition of the present invention can be further combined with any carrier material that preserves the bioactivity of the squalene, linoleic acid and additional fatty acids, if included. Such carrier materials include, but are not limited to resins, liposomes, vesicles, carrier proteins and the like.

II. Routes of Administration

Administration of the pheromone composition to a subject animal is typically accomplished through any method allowing for delivery of a therapeutically effective amount of the pheromone composition via inhalation by the animal. Such methods of administration include, for example, placing or distributing the pheromone composition in the environment of the animal, either by incorporating the composition into a wearable device such as a collar, or by applying (e.g. spraying or wiping) the composition to surfaces in the living environment of the animal or directly onto the animal, such as to its facial region or head. For example, the pheromone composition may be administered topically to an animal using an aerosol, pump spray, foam, collar, wipe, dip, liquid, gel, lotion, and/or cream. The term "therapeutically effective" describes an amount of the pheromone compound that is sufficient to produce a noticeable modification, i.e. improvement, of animal behavior in the subject animal, as determined according to behavioral observations as described herein. The effective amount will depend on factors such as the severity of the behavior being treated; individual animal parameters including age, physical condition, size and weight; concurrent treatments; the frequency of treatment; or the mode of administration. These factors are well known to those of ordinary skill in the art and can be addressed with no more than routine experimentation.

In one embodiment, the pheromone composition in liquid or solid form is incorporated into a solid polymeric formulation to form a collar or tag, and the collar or tag is then worn by the mammal. The solid polymeric formulation generally comprises the pheromone composition as described herein, a carrier, and a low melting polymer or copolymer.

The carrier as used in the solid polymeric formulation of the present invention may be a fatty alcohol or solid fatty alcohol. The fatty alcohol or solid fatty alcohol may comprise any unsaturated or saturated fatty alcohol having from about 6 to about 34 carbon atoms, preferably having from about 11 to about 18 carbon atoms and that is a solid at room temperature. Preferable fatty alcohols include, but are not limited to, cetyl alcohol (which includes: Cetanol, 1-Hexadecanol, Ethal, Ethol, Palmityl alcohol, Hexadecan-1-ol, Hexadecyl alcohol, Hexadecanol, Alcohol C-16, Atalco C, Cachalot C-50, Cetaffine, Cetal, Cetylol, CO-1670, Crodacol-cas, DYTOL F-11, Loroll 24, Loxanol K, and Product 308), stearyl alcohol (which includes: Octadecanol, Stenol, Octadecyl alcohol, Decyl Octyl alcohol, Stearol, N-octadecanol, Adol 68, Alfol 18, Atalco S, CO-1895, CO-1897, Crodacol-S, Dytol E-46, Lorol 28, Polaax, Sipol S, Siponol S, and Steraffine) and Oleyl Alcohol (which includes: Cis-9-Octadecen-1-01). In one embodiment, the solid polymeric formulation comprises a solid fatty alcohol in an amount equal to between about 5% and about 50% by weight of the formulation. In another embodiment, the solid polymeric formulation comprises a solid fatty alcohol in an amount equal to between about 12% and about 30% by weight of the formulation. In a further embodiment, the solid polymeric formulation comprises a solid fatty alcohol in an amount equal to between about 12% and about 25% by weight of the formulation.

Alternatively, the carrier may be a solidifier, such as glycerol monostearate (GMS), which also known as 3-Stearoyloxy-1,2-propanediol; Glyceryl stearate; Alpha-Monostearin; Monostearin; Octadecanoic acid, 2,3-dihydroxypropyl ester; Glycerin 1-monostearate; Glycerin 1-stearate; Glycerol alpha-monostearate; Glyceryl 1-monostearate; Stearic acid alpha-monoglyceride; Stearic acid 1-monoglyceride; 1-Glyceryl stearate; 1-Monostearin; 1-Mono stearoylglycerol; and 1,2,3-Propanetriol 1-octadecanoyl ester.

The low melting polymer or copolymer, which is capable of holding and then releasing the pheromone composition, is selected from those polymers or copolymers that are solid at room temperature and have a melt temperature of below 250° F. In one aspect, the low melting polymer or copolymer has a melt temperature of below 200° F. Examples of polymers and copolymers useful in the solid polymeric formulation of the present invention include, but are not limited to, polyethylene, polyvinyl acetate, ethylene acid copolymers, ethylene acrylates, polyurethanes, styrene-butadiene, polyvinyl acetate, polyvinyl butyral, and mixtures and copolymers thereof. In one embodiment, the solid polymeric formulation comprises a low melting polymer or copolymer in an amount equal to between about 40% and about 85% by weight of the formulation. In another embodiment, the solid polymeric formulation comprises a low melting polymer or copolymer in an amount equal to between about 65% and about 80% by weight of the formulation. In a further embodiment, the solid polymeric formulation comprises a low melting polymer or copolymer in an amount equal to between about 70% and about 75% by weight of the formulation.

Additional components may optionally be included in the solid polymeric formulation of the present invention. Such optional components can include, but are not limited to, plasticizers, synergists, fragrances, coloring agents, preservatives, antioxidants, light stabilizers, and the like.

To prepare the solid polymeric formulations of the present invention, the unsaturated or saturated long chain fatty alcohol is added to a low melting polymer or copolymer and mixed until uniformity is achieved. The pheromone composition is then added with mixing to form a blend. This blend formulation may then be processed into a shaped article or device, such as a pet collar or a tag or the like, on a conventional extruder or molding machine at low temperatures (that is, at a temperature that will melt the low melting polymer or copolymer, which is generally below about 250° F.) using methods known in the art.

After the polymeric formulation is shaped or formed into the desired shape, the article or device, such as a collar, is placed into close proximity with an animal to be treated; that is, the device will be located, by attachment or other means, in sufficient proximity to or contact with the animal such that the pheromone composition will, together with the solid fatty alcohol, be released to the surface of the article as a result of the animal's body heat. The combination of the saturated or unsaturated long chain fatty alcohol and the low-melting polymer allows the pheromone to be released to the surface of the polymeric formulation continuously over a period of at least four weeks while it is simultaneously being transferred to the animal's hair and down to the skin. One skilled in the art will also recognize that the article or device may take other shapes suitable for use with animals in which a collar would be difficult to apply, for example, rodents such as mice and rats. Therefore, for particular animals, the device may take the shape of, for example, a solid strip that can be hung on a wall or from a rafter or ceiling whereby the strip is placed in close proximity to the animal.

In an alternative embodiment, the pheromone composition is combined with a solvent to form a liquid pheromone solution and the liquid pheromone solution be further prepared in various formulations suitable for delivery to the mammal by inhalation. For example, liquid solutions can be further prepared according to methods well known in the art as a spray, gel, foam, shampoo, or spot-on formulation. The pheromone composition is generally solid in nature, but it can also be dissolved or diluted in a nonaqueous organic solvent or solvent mixture to form a pheromone solution. Suitable solvents are generally known within the art and are recognized to include lipophilic organic diluents, alcohols, ethylene glycol, propylene glycol, dipropylene glycol, ether, chloroform, benzene, carbon disulfide, oils including non-volatile and volatile oils, and combinations thereof.

In an exemplary embodiment, the pheromone composition is combined with an organic solvent or solvents and diluents to form a pheromone solution in one of various liquid or liquid-based forms such as sprays, aerosols, gels, dips, shampoos, spot treatments, microencapsulated products and so on. For example, the basic composition can be dissolved in a suitable alcohol and supplied in a liquid form such as a spray or for use in a plug-in diffuser. Suitable alcohols include ethanol, propanol, isopropanol, butanol, pentanol, hexanol, heptanol, octanol, and phenyl ethyl alcohol. In a preferred embodiment, the alcohols comprise ethanol, isopropanol, butanol, and phenyl ethyl alcohol. An alcohol solvent can be combined with a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In a preferred embodiment, the solvent is a combination of dipropylene glycol and an alcohol selected from the group consisting of ethanol, isopropanol, and butanol.

In one exemplary embodiment, the solvent comprises a combination of dipropylene glycol and isopropanol such that the solvent comprises isopropanol in an amount equal to between about 70% and about 90% by volume of the solvent and dipropylene glycol in an amount equal to between about 5% and about 10% by volume of the solvent. The basic pheromone composition is diluted in the solvent to form a pheromone solution wherein the pheromone composition contributes between about 0.5% and about 60% by volume, preferably between about 1% and about 40% by volume, more preferably between about 1% and about 30% by volume, and even more preferably between about 1% and about 15% by volume of the solution.

The concentration of the aforementioned components including squalene, linoleic acid, 1-docosanol, cholesterol and fatty acid mixture, wherein the fatty acids are selected from the group consisting of myristic acid, n-pentadecanoic acid, lauric acid, capric acid, azelaic acid, pimelic acid, and combinations thereof, included in the basic pheromone composition may vary within the aforementioned ranges, depending upon the intended final form and use; however, the total concentration of all components present in the pheromone composition will not exceed 100%. It will be recognized that concentrations of the components that can be used are readily ascertainable and can be assayed according to the behavioral methods set forth herein.

Thus, in one embodiment, the pheromone composition comprises squalene in an amount equal to between about 60% and about 70% by weight, linoleic acid in an amount equal to between about 15% and about 25% by weight, 1-docosanol in an amount equal to between about 1% and about 5% by weight, and a mixture of at least two fatty acids in an amount equal to between about 5% and about 15% by weight, wherein the fatty acids are selected from the group consisting of myristic acid, n-pentadecanoic acid, lauric acid, azelaic acid, pimelic acid, and combinations thereof.

In another embodiment, the basic pheromone composition comprises squalene in an amount equal to between about 20% and about 40% by weight, linoleic acid in an amount equal to between about 55% and about 65% by weight, 1-docosanol in an amount equal to between about 1% and about 10% by weight, and cholesterol in an amount equal to between about 1% and about 10% by weight.

In another embodiment, the pheromone composition comprises squalene in an amount equal to between about 60% and about 70% by weight, linoleic acid in an amount equal to between about 15% and about 25% by weight, 1-docosanol in an amount equal to between about 1% and about 5% by weight, cholesterol in an amount equal to between about 0.1% and about 5% by weight, and a mixture of at least two fatty acids in an amount equal to between about 5% and about 10% by weight, wherein the fatty acids are selected from the group consisting of myristic acid, n-pentadecanoic acid, lauric acid, capric acid, azelaic acid, pimelic acid, and combinations thereof.

In another embodiment, the pheromone composition comprises squalene in an amount equal to between about 20% and about 40% by weight, linoleic acid in an amount equal to between about 55% and about 65% by weight, 1-docosanol in an amount equal to between about 1% and about 5% by weight, cholesterol in an amount equal to between about 0.1% and about 5% by weight, and a mixture at least two fatty acids in an amount equal to between about 2% and about 8% by weight, wherein the fatty acids are selected from the group consisting of myristic acid, n-pentadecanoic acid, lauric acid, and combinations thereof.

In yet another embodiment, the pheromone composition comprises squalene in an amount equal to between about 20% and about 40% by weight, linoleic acid in an amount equal to between about 55% and about 65% by weight, 1-docosanol in an amount equal to between about 1% and about 5% by weight, cholesterol in an amount equal to between about 0.1% and about 5% by weight, and a mixture at least two fatty acids in an amount equal to between about 1% and about 5% by weight, wherein the fatty acids are selected from the group consisting of myristic acid, n-pentadecanoic acid, lauric acid, and combinations thereof.

In one exemplary embodiment the pheromone composition comprises 31% (% w/w) squalene, 59.69% (% w/w) linoleic acid, 2% (% w/w) 1-docosanol, 1% (% w/w) cholesterol, and 6.3% (% w/w) of a mixture of fatty acids, wherein the fatty acids are selected from the group consisting of myristic acid, n-pentadecanoic acid, lauric acid, and combinations thereof.

In a second exemplary embodiment the pheromone composition comprises 67.69% (% w/w) squalene, 20% (% w/w) linoleic acid, 2% (% w/w) 1-docosanol, and 10.3% (% w/w) of a mixture of at least two fatty acids, wherein the fatty acids are selected from the group consisting of myristic acid, n-pentadecanoic acid, lauric acid, capric acid, azelaic acid, pimelic acid, and combinations thereof.

In a third exemplary embodiment the composition comprises 68.19% (% w/w) squalene, 20% (% w/w) linoleic acid, 2% (% w/w) 1-docosanol, 1% (% w/w) cholesterol, and 8.8% (% w/w) of a mixture of at least two fatty acids, wherein the fatty acids are selected from the group consisting of myristic acid, n-pentadecanoic acid, lauric acid, capric acid, azelaic acid, pimelic acid, and combinations thereof.

In a fourth exemplary embodiment the composition comprises 30% (% w/w) squalene, 60% (% w/w) linoleic acid, 4.99% (% w/w) 1-docosanol, and 5% (% w/w) cholesterol.

In a fifth exemplary embodiment the pheromone composition comprises 34% (% w/w) squalene, 61.19% (% w/w) linoleic acid, 2% (% w/w) 1-docosanol, 1% (% w/w) cholesterol, and 1.8% (% w/w) of a mixture of at least two fatty acids, wherein the fatty acids are selected from the group consisting of myristic acid, n-pentadecanoic acid, lauric acid, and combinations thereof.

In a further embodiment, the pheromone composition as disclosed herein is dissolved in a solvent to form a pheromone solution comprising the pheromone composition in an amount equal to between about 1% and about 40% by volume of solution.

In another aspect, the present disclosure encompasses a method of modifying stress-related behavior in a mammal by exposing the mammal to an effective amount of a pheromone composition as disclosed herein. The mammal can be exposed to the pheromone composition by any method allowing inhalation by the mammal (for example, in a collar) over a period of time sufficient to effect a modification of the target behavior, as determined according to behavioral observations. Typically the exposure will be over a period of at least several minutes to a few hours, but can be over a period of days or weeks as may be needed to achieve a satisfactory behavioral effect, and can be continued over a period of weeks, months or longer depending on the particular mammal and situation. For example, a mammal suffering from a temporarily induced anxiety, such as that brought about by a trip to a veterinarian's office, may require a brief exposure to the pheromone composition before, during and/or after the trip to relieve the anxiety and associated behavior. In contrast, a mammal exposed to a stressful stimulus for a longer and continual period, such as a pet exposed to a new pet in the household, may benefit from regular exposure to the pheromone composition.

Following preparation, the pheromone compositions and liquid pheromone solutions thereof can be readily tested for efficacy for stress-relief in mammalian species. Commonly recognized sources of stress in mammals include for example weaning, transportation especially in motorized vehicles, boredom, lack of exercise, separation anxiety, loud noises, introduction to new people or animals and visits to a veterinary office. Mammals that are stressed by exposure to such events or conditions will typically exhibit highly undesirable stress-related behavioral symptoms. Such stress behaviors are commonly recognized and include for example fearful behavior such as cowering or shaking; excessive chewing or barking; hyperactivity; aggressive behavior toward people or other animals such as growling, snappishness or biting; property destruction; and frequent urination or soiling. The efficacy of the pheromone composition can be tested for example by having subject mammals wear a collar incorporating the pheromone composition, or by applying the composition in the form of a liquid spray, liquid diffuser or the like in a physical area associated with the stress-inducing conditions for any given animal. In either case, the pheromone composition is sufficiently volatile for the mammal to inhale and thus be exposed to a sufficient amount of the pheromone composition to produce a noticeable behavioral effect. For example, a reduction in stress-related outward behaviors is readily ascertainable (e.g. noticeable reduction in aggressive displays, barking or chewing) and can be supplemented by observing other physical indicators of stress such heart rate, weight changes, and secretion of stress hormones such as cortisol.

In use, the pheromone composition can be implemented in a number of different ways depending in part on the targeted mammal(s) and behavior to be modified. A liquid solution containing the composition can simply be applied directly to the coat or skin of a mammal, or sprayed on surfaces or objects in the mammal's environment, or diffused or sprayed into the air in the mammal's environment. For example, an exemplary liquid spray solution containing the pheromone composition in an amount equal to between about 1% and about 40% by volume of the solution can be sprayed, for example, on floors, walls or animal toys about once a week, or once or several times daily, as needed, to obtain the desired behavioral modification. Alternatively, for example, a liquid solution containing the pheromone composition in an amount equal to between about 1% and about 15% by volume of the solution can delivered by a diffuser such as a plug-in diffuser commercially available from as Central Life Sciences/Farnam Companies Inc. (Phoenix, Ariz.) as the Comfort Zone® Diffuser (sold with Feliway® or DAP® (Dog Appeasing Pheromone)).

In one embodiment, the composition in liquid or solid form can be incorporated into a solid polymeric formulation as disclosed above, which can then be formed into a tag, or in strips to form a collar suitable for being worn by an animal.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, the terms "about" and "approximately" designate that a value is within a statistically meaningful range. Such a range can be typically within 20%, more typically still within 10%, and even more typically within 5% of a given value or range. The allowable variation encompassed by the terms "about" and "approximately" depends on the particular system under study and can be readily appreciated by one of ordinary skill in the art.

As used herein, the term "w/w" designates the phrase "by weight" and is used to describe the concentration of a particular substance in a mixture or solution.

As used herein, the word "mammal" is interchangeable with the word "animal" and encompasses any group of vertebrates, the females of which have milk-secreting glands, including man. Examples of mammals include, but are not limited to, domestic mammals such as cats and dogs; small mammals, such as hamsters, rabbits, ferrets, rats, mice, and guinea pigs; commercial mammals, such as horses, sheep, cattle, and swine; and mammals in captivity, such as apes, chimpanzees, tigers, lions, bears, elephants, zebras, and the like.

As used herein, the word "stress" refers to the reaction of an animal body to forces of deleterious nature, infections and various abnormal states that tend to disturb homeostasis. This reaction may be a physical reaction or an emotional reaction including anxiety.

As used herein, the word "pheromone" refers to a substance released by the body of a particular species that causes a predictable reaction by another individual of the same species, which substance may serve, for example, as a specific attractant, social communicator, sexual stimulant and the like.

Although the invention described herein is susceptible to various modifications and alternative iterations, specific embodiments thereof have been described in greater detail above. It should be understood that the invention is intended to cover all modifications, equivalents, and alternatives falling within the spirit and scope of the invention as defined by the claim language.

EXAMPLES

Example 1

Pheromone Compositions

Table 1 lists the formulations of five exemplary pheromone compositions (A, B, C, D, and E) prepared according to the present teachings. All amounts are presented as % w/w or by weight of the composition.

TABLE 1

| COMPONENT | FORMULATION (% w/w) | | | | |
| --- | --- | --- | --- | --- | --- |
|  | A | B | C | D | E |
| Linoleic Acid | 59.69 | 20.00 | 20.00 | 60.00 | 61.19 |
| Myristic Acid | 1.50 | 1.50 | 1.00 |  | 1.00 |
| n-Pentadecanoic acid (Pentadecyclic Acid) | 4.50 | 5.50 | 1.50 |  | 0.50 |
| Cholesterol | 1.00 |  | 1.00 | 5.00 | 1.00 |
| Laurie Acid | 0.30 | 0.30 | 0.30 |  | 0.30 |
| 1-Docosanol (Behenyl alcohol or Docosyl Alcohol) | 2.00 | 2.00 | 2.00 | 4.99 | 2.00 |
| Squalene (Shark Origin) | 31.00 | 67.69 | 68.19 | 30.00 | 34.00 |
| Capric Acid |  |  | 4.00 |  |  |
| Azelaic Acid |  | 1.50 | 1.00 |  |  |
| BHT | 0.01 | 0.01 | 0.01 | 0.01 | 0.01 |
| Pimelic Acid (Heptanedioic acid) |  | 1.50 | 1.00 |  |  |
| TOTAL | 100.00 | 100.00 | 100.00 | 100.00 | 100.00 |

Example 2

Liquid Pheromone Solutions

Table 2 lists three liquid formulations (F, G, and H) of the pheromone composition according to the present teachings. As is shown, each liquid formulation consists of a pheromone "concentrate" composition consisting primarily of squalene and linoleic acid, plus 1-docosanol, cholesterol, additional fatty acids and BHT. The pheromone composition contributed 15.1% by volume to the final volume of each liquid formulation, after the mostly solid pheromone "concentrate" was dissolved in a mixture of dipropylene glycol and an alcohol (ethanol 190 proof (90%), isopropanol, or butanol). All amounts listed below are presented as % v/v.

TABLE 2

| COMPONENT | FORMULATION (% v/v) | | |
|---|---|---|---|
| | F | G | H |
| Dipropylene Glycol | 7.17800 | 7.17800 | 7.17800 |
| Ethanol 190 proof (90%) | 77.60000 | | |
| Isopropanol | | 77.60000 | |
| Butanol | | | 77.60000 |
| Linoleic Acid | 9.36200 | 9.36200 | 9.36200 |
| Myristic Acid | 0.15100 | 0.15100 | 0.15100 |
| n-Pentadecanoic acid (Pentadecyclic Acid) | 0.07550 | 0.07550 | 0.07550 |
| Cholesterol | 0.15100 | 0.15100 | 0.15100 |
| Lauric Acid | 0.04530 | 0.04530 | 0.04530 |
| 1-Docosanol (Behenyl alcohol or Docosyl Alcohol) | 0.30200 | 0.30200 | 0.30200 |
| Squalene (Shark Origin) | 5.13400 | 5.13400 | 5.13400 |
| Capric Acid | | | |
| Azelaic Acid | | | |
| BHT | 0.00151 | 0.00151 | 0.001510 |
| Pimelic Acid (Heptanedioic acid) | | | |
| TOTAL | 100.00000 | 100.00000 | 100.00000 |

Example 3

Preparation of Solid Polymeric Formulation

The solid polymeric formulation in Table 3 (below) is prepared using any one of the pheromone compositions set forth in Example 1, and is then formed into an animal collar, as follows:

TABLE 3

| COMPONENT | WEIGHT (grams) | FORMULATION (%) |
|---|---|---|
| Pheromone Composition | 6.0 | 6.0 |
| Cetyl Alcohol (Procter & Gamble) | 20.0 | 20.0 |
| Microthene ® Polymer MU-76000 (Equistar Chemicals, LP) | 73.8 | 73.8 |
| Lime Green Colorant (Day Glow Color Corp.) | 0.2 | 0.2 |
| TOTAL | 100.0 grams | 100.0% |

Microthene ® Polymer MU-76000 (ethylene-vinyl acetate copolymer, vinyl acetate content: 18 wt %, ground powder, melt index: 32 g/10 min (EMI), avg. particle size: 35 mesh) - Equistar Chemicals, LP.

The polymer was weighed and placed into a mixing vessel. The colorant was added to the polymer with mixing. The cetyl alcohol was added to the polymer and mixed until uniform. The pheromone composition prepared in accordance with Example 1 was added to the polymer/fatty alcohol mixture while mixing, and mixing continued for 1-2 hours. The resulting blend was allowed to cool to room temperature, preferably overnight, which allowed for easy feeding of the blend while extruding.

The blend was extruded using temperature settings at 190° F. for zones 1, 2, 3 and 4, into the desired shape, which for purposes of this Example 3 was an animal collar for use on any animal described in the present invention, including companion animals or livestock.

Example 4

Solid Polymeric Formulations

Following the procedures in Example 3, animal collars were prepared from each of the formulations in Tables 4-9, below.

TABLE 4

| COMPONENT | WEIGHT (grams) | FORMULATION (%) |
|---|---|---|
| Pheromone Composition | 6.0 | 6.0 |
| Cetyl Alcohol (Procter & Gamble) | 20.0 | 20.0 |
| Microthene ® Polymer MU-76000 (Equistar Chemicals, LP) | 70.8 | 70.8 |
| Lime Green Colorant (Day Glow Color Corp.) | 0.2 | 0.2 |
| Fragrance | 3.0 | 3.0 |
| TOTAL | 100.0 grams | 100.0% |

TABLE 5

| COMPONENT | WEIGHT (grams) | FORMULATION (%) |
|---|---|---|
| Pheromone Composition | 6.0 | 6.0 |
| Cetyl Alcohol (Procter & Gamble) | 12.5 | 12.5 |
| Microthene ® Polymer MU-76000 (Equistar Chemicals, LP) | 78.3 | 78.3 |
| Lime Green Colorant (Day Glow Color Corp.) | 0.2 | 0.2 |
| Fragrance | 3.0 | 3.0 |
| TOTAL | 100.0 grams | 100.0% |

TABLE 6

| COMPONENT | WEIGHT (grams) | FORMULATION (%) |
|---|---|---|
| Pheromone Composition | 9.0 | 9.0 |
| Cetyl Alcohol (Procter & Gamble) | 20.0 | 20.0 |
| Microthene ® Polymer MU-76000 (Equistar Chemicals, LP) | 70.8 | 70.8 |
| Lime Green Colorant (Day Glow Color Corp.) | 0.2 | 0.2 |
| TOTAL | 100.0 grams | 100.0% |

TABLE 7

| COMPONENT | WEIGHT (grams) | FORMULATION (%) |
|---|---|---|
| Pheromone Composition | 9.0 | 9.0 |
| Cetyl Alcohol (Procter & Gamble) | 20.0 | 20.0 |
| Microthene ® Polymer MU-76000 (Equistar Chemicals, LP) | 67.8 | 67.8 |
| Lime Green Colorant (Day Glow Color Corp.) | 0.2 | 0.2 |

TABLE 7-continued

| COMPONENT | WEIGHT (grams) | FORMULATION (%) |
|---|---|---|
| Fragrance | 3.0 | 3.0 |
| TOTAL | 100.0 grams | 100.0% |

TABLE 8

| COMPONENT | WEIGHT (grams) | FORMULATION (%) |
|---|---|---|
| Pheromone Composition | 9.0 | 9.0 |
| Cetyl Alcohol (Procter & Gamble) | 12.5 | 12.5 |
| Microthene ® Polymer MU-76000 (Equistar Chemicals, LP) | 75.3 | 75.3 |
| Lime Green Colorant (Day Glow Color Corp.) | 0.2 | 0.2 |
| Fragrance | 3.0 | 3.0 |
| TOTAL | 100.0 grams | 100.0% |

TABLE 9

| COMPONENT | WEIGHT (grams) | FORMULATION (%) |
|---|---|---|
| Pheromone Composition | 6.0 | 6.0 |
| Glycerol Monostearate (GMS) | 16.0 | 16.0 |
| Microthene ® Polymer MU-76000 (Equistar Chemicals, LP) | 74.8 | 74.8 |
| Lime Green Colorant (Day Glow Color Corp.) | 0.2 | 0.2 |
| Fragrance | 3.0 | 3.0 |
| TOTAL | 100.0 grams | 100.0% |

Example 5

Efficacy Study of a Pheromone Collar on Dogs

The primary objective of this study was to assess the efficacy of a pheromone collar comprising a pheromone composition of the present invention in controlling stress-related behaviors in dogs. The solid polymeric formulation was made and formed into a collar in accordance with the process set forth in Example 3, which formulation incorporated the pheromone composition noted as Formula C in Example 1. All of the dogs enrolled in the study were client-owned dogs presented to a veterinary practice for behavior-related problems. Owners were invited to participate in the study if the dog exhibited one or more of the following symptoms: nervousness or fear of noise; timidity/fear of other dogs or people; excessive chewing; excessive barking; aggressive displays toward other dogs or the owner; soiling when left alone; destructive; dislike of being touched/handled; and/or hyperactivity. The dogs remained in their home environments for the duration of the test period. The testing period lasted anywhere from one to three months. Animal subjects acted as their own controls.

Nineteen dogs were enrolled in the study. Two animals were excluded from the final data analysis, leaving data from a total of seventeen animals. The two excluded animals shared a household and each managed to detach the other's collar shortly after the collars were applied.

Behavioral characteristics of the subject dogs are set forth in Table 10 below.

TABLE 10

| DOG ID | DOG NAME | DOG BREED | AGE | TYPE OF BEHAVIOR DISORDER |
|---|---|---|---|---|
| 1 | Neeko | Rottweiler Border Collie Cross | 9 months old | Nervous of noises, timid with other dogs and people. |
| 2 | Riddick | Rottweiler | 2 year old | Nervous of noises and hyperactive in the house. |
| 3 | Rosie | Staffie | 2 1/2 year old | Barked at everything through the window and was hyperactive. |
| 4 | Rufus | Staffie | 2 year old | Very nervous and timid and shied away from other dogs. |
| 5 | Dixie | Staffie cross | 1 year old | Very hyperactive, over the top playful and chewed a lot. |
| 6 | Tyson | American Mastiff | 8 year old | Soiling. Very smelly dog. |
| 7 | Murphy | Cocker Spaniel | 1 year old | Very hyperactive and soiling/smelly. |
| 8 & 9 | Buster and Barney | Border Terriers | Both 2 years old | Destructive house |
| 10 | Diesel | Collie cross with Belgian Sheppard | 7 months old | Very snappy with owners, did not like to be fussed with or touched. |
| 11 | Artimakay | Deerhound | 5 months old | Constantly barking at owner for attention |
| 12 | Herby | Wirehaired Dachshund | 3 years old | Soiling/Toileting when left alone. |
| 13 | Millie | Terrier | 2 years old | Very nervous of people and big dogs. |
| 14 | Benji | Yorkshire Terrier | 1 1/2 years old | Did not like men and was nervous of other dogs. |
| 15 | Bailey | Chocolate Labrador | 11 months old | Nervous of people he did not know and some dogs. |
| 16 | Bigun | German Sheppard cross Retriever | 9 years old | Easily stressed leading to hyperactivity |
| 17 | Mutley | Cross breed | 15 year old | Senile barking (deaf and nearly blind) |
| 18 | Piglet | Terrier cross | 4 years old | Easily stressed and suffers from polydipsia (over drinking) and polyuria (urinating excessively) |
| 19 | Dobbie | Cross breed | 9 year old | Some instances of aggressive behavior |

As illustrated in FIG. 1, after the collars were applied to the dogs, 77% of the treated dogs exhibited a positive behavior response to the pheromone collar (i.e., 13 out of 17 dogs displayed one or more of the following: were more relaxed, stopped trembling, regained confidence, stopped being hyperactive, showed great improvement when dealing with others, appeared happier, and stopped barking excessively).

After four weeks the collars were removed from the dogs. A majority of the dogs reverted back to being nervous (trembling) and timid, hyperactive, and displaying excessive barking.

During the 3-month testing period, visible evidence was observed as to the functionality of the collars of the present invention. The majority of the testing subjects exhibited positive results after using the collar and most regressed to their previous behaviors once its use was suspended.

Example 6

Efficacy of a Pheromone Collar on Cats

The primary objective of this study was to assess the efficacy of a pheromone collar comprising a pheromone composition of the present invention in controlling stress-related behaviors in cats. Cat owners were recruited at random from a database of known cat owners. Cats qualified for the study if they exhibited one or more of the problem behaviors at least twice weekly with a nuisance factor (for the owners) of at least 6 on a 10-point scale: vertical scratching, urine marking, hissing, hiding, aggression towards people and/or other animals, and excessive meowing. Cats were at least six months old. Age, weight, and short hair vs. long hair were recorded, but were not screening factors.

119 cats were selected to participate in the study. The selected cats were divided into two treatment groups. Animals from the first group were treated with a pheromone collar which was worn around the neck for a period of thirty days. The solid polymeric formulation was made and formed into a collar in accordance with process set forth in Example 3, using the polymeric formulation provided in Table 6, which incorporated the pheromone composition noted as Formula C in Example 1. Animals from the second group were treated using a commercial plug-in cat pheromone diffuser (Comfort Zone® diffuser sold by Feliway®) for a period of two months. The study was conducted under blind conditions so that the human owners did not know the identity of the brand name, manufacturer name and composition during the course of the study. Owners were asked to answer simply "Yes" or "No" as to whether any improvement in behavior was noticed during the course of the two-month treatment period.

Among collar users with multiple cats, 44% noticed a calming effect, vs. 29% of users with only one cat. In addition, 35% of collar users with multiple cats noticed better behavior in their cats with dogs and/or other cats and 26% of collar users with multiple cats reported reduced or eliminated aggression, vs. 13% and 7%, respectively, of collar users with only one cat. Among all of the subjects, over 20% of collar users rated the collars as "excellent", compared to only 3% of diffuser users; and 68% of the collar users reported positive comments about behavioral efficacy, compared to 44% of the diffuser users.

Figure 2:
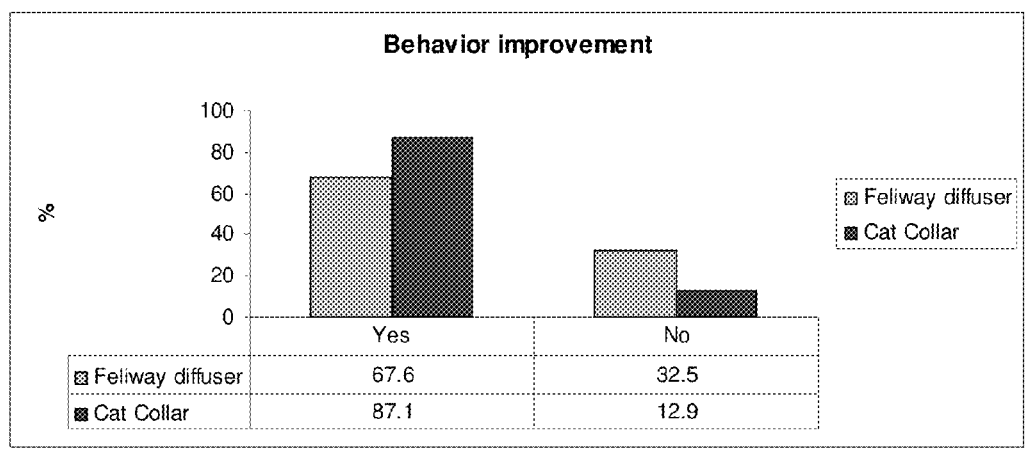
FIG. 2 is a bar graph illustrating the behavioral results obtained in a clinical field trial of a pheromone composition on cats exhibiting behavior problems.

FIG. 2 is a bar graph summarizing the results of the study and illustrating that the majority of cat owners reported noticeable behavior improvement using the composition of the present invention both in the collar and in the diffuser. Results were statistically significant at 1%.

Example 7

Efficacy of a Pheromone Collar on Horses

Collars prepared in accordance with Example 3 and their efficacy on horses was tested and assessed. It was observed that when a collar of the present invention was placed in close proximity to a horse, the horse appeared to be more relaxed than prior to being subjected to the pheromone collar.

While the invention has been explained in relation to exemplary embodiments, it is to be understood that many variations, modifications, and changes to the process described herein are possible and will become apparent to those skilled in the art upon reading the description. Therefore, it is to be understood the invention disclosed herein is intended to cover such variations, modifications, and changes which do not depart from the spirit and scope of the present invention, which invention is limited only by the claims which follow.

One skilled in the art would readily appreciate that the methods and compositions described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A polymeric formulation for controlled delivery of a pheromone, the polymeric formulation comprising: a low melting polymer or copolymer; a carrier; and a pheromone composition comprising squalene, linoleic acid, and 1-docosanol, wherein the pheromone composition does not contain either palmitic acid or oleic acid.

2. The polymeric formulation according to claim 1, wherein the pheromone composition comprises between about 20% and about 40% by weight of squalene, between about 50% and about 70% by weight of linoleic acid, and between about 1% and about 10% by weight of 1-docosanol.

3. The polymeric formulation according to claim 1, wherein the pheromone composition comprises between about 50% and about 70% by weight of squalene, between about 10% and about 30% by weight of linoleic acid, and between about 1% and about 10% by weight of 1-docosanol.

4. The polymeric formulation according to claim 1, wherein the pheromone composition further comprises between about 0.1% and about 10% by weight of cholesterol.

5. The polymeric formulation according to claim 1, wherein the pheromone composition further comprises between about 1% and about 15% by weight of a mixture of at least two fatty acids, wherein the fatty acids are selected from the group consisting of myristic acid, n-pentadecanoic acid, lauric acid, capric acid, azelaic acid, pimelic acid, and combinations thereof.

6. The polymeric formulation according to claim 1, wherein the pheromone composition is present in the polymeric formulation in an amount equal to between about 0.3% to about 20% by weight of the formulation.

7. The polymeric formulation according to claim 1, wherein the low melting polymer or copolymer is selected from the group consisting of polyethylene, polyvinyl acetate, ethylene acid copolymers, ethylene acrylates, polyurethanes, styrene-butadiene, polyvinyl butyral, and combinations thereof, and wherein the low melting polymer or copolymer is present in the polymeric formulation in an amount between about 40% to about 85% by weight of the polymeric formulation.

8. The polymeric formulation according to claim 1, wherein the carrier is glycerol monostearate.

9. The polymeric formulation according to claim 1, wherein the carrier is a saturated or unsaturated long-chain fatty alcohol having from about 6 to about 34 carbon atoms.

10. The polymeric formulation according to claim 9, wherein the long-chain fatty alcohol is selected from the group consisting of cetyl alcohol, stearyl alcohol, and oleyl alcohol, and wherein the long-chain fatty alcohol is present in the polymeric formulation in an amount from about 5% to about 50% by weight of the formulation.

11. The polymeric formulation according to claim 1, wherein the polymeric formulation is shaped into a collar.

12. The polymeric formulation according to claim 11, wherein the collar is suitable for a mammal.

13. The polymeric formulation according to claim 12, wherein the mammal is selected from the group consisting of cats, dogs, horses, cattle, pigs, rats, rabbits, apes, and chimpanzees.

14. A polymeric formulation for controlling behavior in mammals, the formulation comprising a low melting polymer or copolymer, a carrier, and a pheromone composition comprising between about 20% and about 40% (% w/w) squalene, between about 50% and about 70% (% w/w) linoleic acid, and between about 1% and about 10% (% w/w) 1-docosanol, wherein the pheromone composition does not contain either palmitic acid or oleic acid.

15. The polymeric formulation according to claim 14, wherein the pheromone composition is present in the polymeric formulation in an amount from about 5% to about 10% by weight of the formulation.

16. The polymeric formulation according to claim 14, wherein the low melting polymer or copolymer is selected from the group consisting of polyethylene, polyvinyl acetate, ethylene acid copolymers, ethylene acrylates, polyurethanes, styrene-butadiene, polyvinyl butyral, and combinations thereof, and wherein the low melting polymer or copolymer is present in the polymeric formulation in an amount from about 40% to about 85% of the total weight of the formulation.

17. The polymeric formulation according to claim 14, wherein the carrier is glycerol monostearate.

18. The polymeric formulation according to claim 14, wherein the carrier is a saturated or unsaturated long-chain fatty alcohol having from about 6 and 34 carbon atoms.

19. The polymeric formulation according to claim 18, wherein the long-chain fatty alcohol is selected from the group consisting of cetyl alcohol, stearyl alcohol, and oleyl alcohol, and wherein the long-chain fatty alcohol is present in the polymeric formulation in an amount from about 12% to about 30% by weight of the formulation.

20. The polymeric formulation according to claim 14, wherein the polymeric formulation is shaped into a collar.

21. The polymeric formulation according to claim 20, wherein the collar is suitable for a mammal.

22. The polymeric formulation according to claim 21, wherein the mammal is selected from the group consisting of cats, dogs, horses, cattle, pigs, rats, rabbits, apes, and chimpanzees.

23. A polymeric formulation for controlling behavior in mammals, the formulation comprising a low melting polymer or copolymer, a carrier, and a pheromone composition comprising between about 50% and about 70% (% w/w) squalene, between about 10% and about 30% (% w/w) linoleic acid, and between about 1% and about 10% (% w/w) 1-docosanol, wherein the pheromone composition does not contain either palmitic acid or oleic acid.

24. A polymeric formulation for controlling behavior in mammals, the formulation comprising a low melting polymer or copolymer, a carrier, and a pheromone composition comprising squalene, linoleic acid, 1-docosanol, cholesterol and a mixture of at least two fatty acids selected from the group consisting of myristic acid, n-pentadecanoic acid, lauric acid, capric acid, azelaic acid, pimelic acid, and combinations thereof, wherein the pheromone composition does not contain either palmitic acid or oleic acid.

25. A method for calming stress-related behavior in mammals, the method comprising the step of placing a polymeric formulation for controlling behavior in mammals in close proximity with a mammal to be treated, wherein the polymeric formulation comprises a low melting polymer or copolymer, carrier, and a pheromone composition comprising between about 50% and about 70% (% w/w) squalene, between about 10% and about 30% (% w/w) linoleic acid, and between about 1% and about 10% (%/w) 1-docosanol, wherein the pheromone composition does not contain either palmitic acid or oleic acid.

26. The method according to claim 25, wherein the polymeric formulation is shaped into a collar.

27. The method according to claim 26, wherein the collar is suitable for a mammal.

28. The method according to claim 27, wherein the mammal is selected from the group consisting of cats, dogs, horses, cattle, pigs, rats, rabbits, apes, and chimpanzees.

29. A method for preparing a polymeric formulation for the control of animal behavior, the method comprising the steps of:
a. mixing a low melting polymer or copolymer with a carrier;
b. adding a pheromone composition to the low melting polymer and fatty alcohol to form a polymeric blend, wherein the pheromone composition comprises between bout 50% and about 70% (% w/w) squalene, between about 10% and about 30% (% w/w) linoleic acid, and between about 1% and about 10% (% w/w) 1-docosanol, wherein the pheromone composition does not contain palmitic acid or oleic acid;
c. processing the polymeric blend at a temperature at or below 250° F.; and
d. forming the polymeric blend into a shaped article or device.

30. The method according to claim 29, wherein the shaped article or device is a collar.

31. The method according to claim 30, wherein the collar is suitable for a mammal.

32. The method according to claim 31, wherein the mammal is selected from the group consisting of cats, dogs, horses, cattle, pigs, rats, rabbits, apes, and chimpanzees.

* * * * *